(12) United States Patent
Garlough

(10) Patent No.: US 8,524,097 B2
(45) Date of Patent: *Sep. 3, 2013

(54) PLASMA DEPOSITION TO INCREASE ADHESION

(75) Inventor: Greg Garlough, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 1017 days.

This patent is subject to a terminal disclaimer.

(21) Appl. No.: 12/406,442

(22) Filed: Mar. 18, 2009

(65) Prior Publication Data

US 2010/0236684 A1    Sep. 23, 2010

(51) Int. Cl.
*C03C 15/00*    (2006.01)

(52) U.S. Cl.
USPC ............................ 216/33; 216/34; 216/36

(58) Field of Classification Search
USPC ............................................ 216/33, 34, 36
See application file for complete search history.

(56) References Cited

U.S. PATENT DOCUMENTS

| | | | |
|---|---|---|---|
| 4,335,238 A | 6/1982 | Moore et al. | |
| 4,743,327 A | 5/1988 | DeHaan et al. | |
| 4,913,762 A | 4/1990 | Kittler | |
| 4,933,060 A | 6/1990 | Prohaska et al. | |
| 4,999,215 A | 3/1991 | Akagi et al. | |
| 5,376,400 A | 12/1994 | Goldberg et al. | |
| 5,425,832 A * | 6/1995 | Kusano et al. | 156/272.6 |
| 5,500,257 A | 3/1996 | Krause et al. | |
| 5,798,146 A | 8/1998 | Murokh et al. | |
| 6,052,625 A | 4/2000 | Marshall | |
| 6,263,249 B1 | 7/2001 | Stewart et al. | |
| 6,306,165 B1 | 10/2001 | Patnaik et al. | |
| 6,506,457 B2 | 1/2003 | Hum | |
| 6,517,657 B1 | 2/2003 | Kuenzel et al. | |
| 6,549,811 B2 | 4/2003 | Stewart et al. | |
| 6,613,432 B2 | 9/2003 | Zamora et al. | |
| 6,649,005 B1 | 11/2003 | Jing et al. | |
| 6,803,069 B2 | 10/2004 | Patnaik et al. | |
| 7,285,132 B2 | 10/2007 | Tseng et al. | |
| 2001/0044655 A1 | 11/2001 | Patnaik et al. | |
| 2002/0104751 A1 | 8/2002 | Drewery et al. | |
| 2002/0133072 A1 | 9/2002 | Wang et al. | |
| 2003/0023190 A1 | 1/2003 | Cox | |
| 2004/0047909 A1 | 3/2004 | Ragheb et al. | |
| 2004/0070309 A1 | 4/2004 | Nomura et al. | |
| 2004/0181278 A1 | 9/2004 | Tseng et al. | |
| 2005/0048218 A1 | 3/2005 | Weidman | |
| 2006/0009829 A1 * | 1/2006 | Aron et al. | 607/122 |
| 2007/0202144 A1 | 8/2007 | Hellerbrand et al. | |
| 2007/0237945 A1 | 10/2007 | Ohrlander et al. | |

(Continued)

OTHER PUBLICATIONS

Kogelschatz, Ulrich. Dielectric-barrier Discharges: Their History, Discharge Physics, and Industrial Applications. *Plasma Chemistry and Plasma Processing*. Mar. 2003;203(1)1-46.

(Continued)

*Primary Examiner* — Binh X Tran
(74) *Attorney, Agent, or Firm* — Carol F. Barry

(57) ABSTRACT

Plasma etching of a liquid dielectric material such as a polyurethane solution results in volatile byproducts that are deposited onto the surface of an inert substrate. The surface treatment increases adhesiveness so that the surface of the inert material may be bonded to another material. Portions of a medical device comprising an inert substrate such as a fluoropolymer may therefore be securely affixed to other portions of the medical device formed of polymeric, metallic, or ceramic materials.

20 Claims, 1 Drawing Sheet

(56) References Cited

U.S. PATENT DOCUMENTS

| | | |
|---|---|---|
| 2008/0075832 A1 | 3/2008 | Abi Aoun |
| 2008/0118734 A1 | 5/2008 | Goodwin et al. |
| 2008/0200434 A1 | 8/2008 | Daniloff |
| 2009/0148591 A1* | 6/2009 | Wang et al. ............... 427/2.25 |
| 2009/0220794 A1* | 9/2009 | O'Neill et al. ............... 428/414 |

OTHER PUBLICATIONS

Schuetze, Andreas, et al. The Atmospheric-Pressure Plasma Jet: A Review and Comparison to Other Plasma Sources. *IEEE Transactions on Plasma Science*. Dec. 1998;26(6):1685-1694.

* cited by examiner

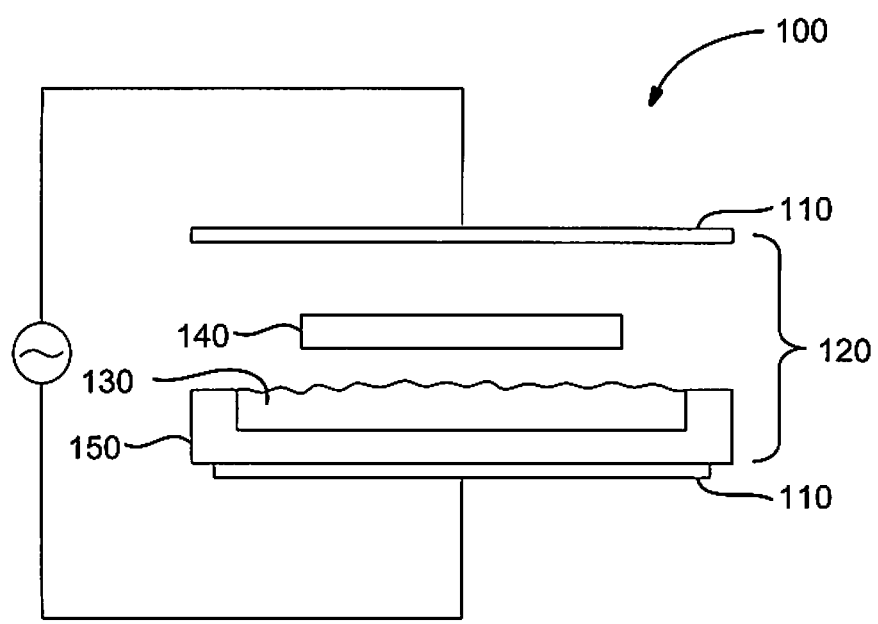

PLASMA DEPOSITION TO INCREASE ADHESION

INTRODUCTION

The present technology relates to increasing the adhesiveness of an inert substrate, such as a fluoropolymer.

Fluoropolymers, also described as fluorine-containing polymers or fluorinated polymers, are an important class of polymers that include fluoroelastomers and fluoroplastics, where part or all of the hydrogen has been replaced by fluorine. Among this broad polymer class are polymers of high thermal stability, polymers exhibiting chemical and solvent resistance, and polymers displaying usefulness along a broad spectrum of temperatures. Many of these polymers are also almost totally insoluble in a wide variety of organic solvents. Fluoroelastomers, particularly copolymers of vinylidene fluoride with other ethylenically unsaturated halogenated monomers, such as hexafluoropropylene, are useful in high temperature applications. Fluoroplastics, particularly polychlorotrifluoroethylene, polytetrafluoroethylene, copolymers of tetrafluoroethylene and hexafluoropropylene, and poly(vinylidene fluoride), have numerous electrical, mechanical, and chemical applications. Fluoroplastics are useful in wire coatings, electrical components, seals, solid and lined tubing and piping, and piezoelectric detectors. Multi-layer constructions containing one or more fluoropolymers also enjoy similar applications.

In general, fluoropolymers have an impressive array of engineering properties including outstanding temperature and chemical resistance. These properties make them a good choice for use in a variety of polymer applications including medical, industrial, electronic, and specialty engineering areas. In addition, many fluoropolymers have a very low coefficient of friction and this can be useful in many applications as a non-stick surface. However, this non-stick attribute creates other difficulties when it is necessary to coat, print, or bond these materials due to their extremely low surface energy. Affixing a fluoropolymer to another material, or vice versa, often provides a considerable challenge as the same advantageous chemical and physical properties of fluoropolymers often make them notoriously difficult to adhere to another material, including other polymers, metals, and ceramics. In many cases it is nearly impossible to achieve adequate adhesion without some type of surface preparation.

Various chemical and physical constructions have been used to improve adhesion between fluoropolymers and other materials. In some cases, the fluoropolymer is co-extruded with another polymer to make a multi-layer construction or composite. Other methods involve using an adhesive layer between the fluoropolymer and other material. Blends of the fluoropolymer and the dissimilar material have also been employed as an intermediate layer to help bond the two layers together, although incompatibilities between materials may make it difficult to form a stable laminate. Addition of a bonding agent, such as a tie layer, which comprises a dissimilar, non-fluorinated polymer, may also be used to increase adhesion between the fluoropolymer and non-fluorinated layer. Such methods generally employ fluoropolymers and non-fluorinated polymers having some measure of chemical reactivity with the tie layer in order to achieve an acceptable level of adhesiveness. Unfortunately some polymers may exhibit a significant change in physical properties when employed as part of a tie layer, where for example, degradation in melt viscosity can make it prohibitively difficult to co-process the multiple layers of materials.

Surface treatment of one or both of the fluoropolymer and other material is also employed to aid bonding and improve adhesion. For example, fluoropolymer layers have been treated with a charged gaseous atmosphere (e.g., corona treatment) prior to bonding of the second material. Another surface treatment used includes cleaning the fluoropolymer surface with solvent, for example with acetone or methyl ethyl ketone, followed by physical abrasion, and then chemically etching using a solution prepared by mixing sodium metal, naphthalene, and tetrahydrofuran. However, these surface treatment methods are aggressive and may degrade the physical properties of the fluoropolymer, may leave undesirable surface residues, and may discolor the polymer surface, which may be undesirable for some purposes.

Medical devices may be coated with fluoropolymers in order reduce sliding friction (e.g., by providing lubricity) and provide other performance enhancing characteristics such as chemical inertness and biocompatibility. For example, applying fluoropolymer coatings to insertable medical devices imparts lubricity and lowers the coefficient of friction for the outer surface of the device. Some of these fluoropolymer coatings, such as polytetrafluoroethylene, are used to provide a lubricious hydrophobic surface. However, obtaining adequate adherence of the fluoropolymer to another portion of the medical device or instrument, be it another polymer, metal, or ceramic, or obtaining adequate adherence of a subsequent polymer layer or other material over the fluoropolymer are common problems.

A need, therefore, exists for methods that improve adhesiveness of inert substrates, such as fluoropolymer substrates, and articles produced thereby.

SUMMARY

The present technology includes systems, methods, articles, and compositions that relate to increasing the adhesiveness of the surface of an inert substrate. Methods of increasing adhesiveness of an inert substrate include etching a dielectric material with plasma, where at least a portion of the dielectric material comprises polyurethane, to form volatile byproducts. The volatile byproducts are deposited onto at least a portion of the surface of the inert substrate, thereby increasing adhesiveness of the inert substrate surface for bonding to other materials.

The present technology also includes methods for bonding an inert substrate to a second substrate. A dielectric material may be etched with plasma, where at least a portion of the dielectric material comprises polyurethane, in order to form volatile byproducts. The volatile byproducts are deposited onto at least a portion of the surface of the inert substrate. An adhesive may be applied to at least a portion of the surface of the inert substrate having deposited volatile byproducts and/or at least a portion of the surface of the material. The inert substrate and the material are coupled via the adhesive.

The present technology also includes substrates and articles produced according to the present methods. An inert substrate competent for bonding to another material has a surface treatment formed according to the processes described herein. A multilayer article comprising a first inert substrate adhesively bonded to a second substrate may be formed according to the processes described herein.

DRAWINGS

The drawings described herein are for illustrative purposes only of selected embodiments and not all possible implementations, and are not intended to limit the scope of the present disclosure.

FIG. 1 illustrates a cross-sectional view of an embodiment of a dielectric barrier discharge apparatus.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the apparatus and systems of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. In addition, disclosure of ranges includes disclosure of all distinct values and further divided ranges within the entire range.

The present technology relates to improving adhesion and bonding of materials together, wherein at least one of the materials may be made of an inert substrate such as a fluoropolymer. By virtue of the present technology, it is possible to increase the adhesiveness of inert substrates to improve bonding of other materials thereto while avoiding any destructive treatment of the inert substrate. More particularly, the present methods and multi-layered substrates produced thereby use a thin plasma deposition layer or coating adhered to the surface of the inert substrate, such as a fluoropolymer substrate. This thin plasma deposition layer or coating may be formed from plasma etching of a polymeric fixture, such as a polyurethane fixture within or part of a plasma reaction chamber. As the plasma etches the polyurethane fixture, some of the polyurethane material may be deposited onto the inert substrate. The deposited layer or coating serves to increase the adhesive potential between the surface of the inert substrate and another material. An adhesive composition or tie layer may also be used to bond the coated inert substrate to another material, where the deposited layer or coating improves bonding to the adhesive composition or tie layer. The other material may be one that is readily adhered to by the adhesive composition or may be another inert substrate that has a plasma deposited coating.

The utilization of substrates having an inert surface made of a material such as fluoropolymers or the like, particularly polytetrafluoroethylene (PTFE) resins (e.g., Teflon®), is an important part of certain industries and can be especially important in the medical implant industry in connection with devices having surfaces that must be chemically inert. Chemically inert surfaces are those which are extremely resistant to chemical interaction except under the most stringent of conditions. Such inert surfaces are particularly useful because they effectively resist chemical interaction under conditions in which it is important that the surface of the substrate maintains its integrity during use, such as in situations where the surface may be intended for contact with corrosive materials. Other situations include those where the material that contacts the inert surface cannot tolerate the presence of foreign materials, such as where the inert surface contacts body tissue or fluids.

The beneficial properties of chemical inertness present a substantial problem when it becomes necessary to rigidly affix an inert substrate to the surface of a different material or to another inert substrate. Heretofore, the bonding of an inert substrate such as a fluoropolymer often required an approach whereby the inert surface to be bonded is destructively treated by harsh procedures, for example chemical etching with a powerful etchant such as sodium metal dissolved in tetrahydrofuran and naphthalene, which removes a surface layer of the inert material and activates the inert surface.

In contrast, the present methods utilize plasma to etch material (e.g., polyurethane) from a fixture of the plasma system, such as a fixture comprising at least part of or contained within a plasma reaction chamber, where the etched and volatilized material may then be deposited to form a thin layer or coating on an inert substrate placed within the reaction chamber. Plasma, the fourth state of matter, is a partially ionized gas composed of ions, electrons, and neutral species. This state of matter is produced by high temperatures and/or strong electric fields created by constant or pulsed DC current, AC current, or time varying (e.g., R.F. or microwave)

electromagnetic fields. Discharge plasmas are produced when free electrons are energized by electric fields in a background of neutral atoms/molecules. These electrons cause electron-atom/molecule collisions which transfer energy to the atoms/molecules and form a variety of species which may include photons, metastables, atomic excited states, free radicals, molecular fragments, monomers, electrons, and ions. The neutral gas becomes partially (or fully) ionized and is able to conduct currents.

Plasma surface treatment typically refers to a plasma reaction that either results in modification of the molecular structure of the surface or atomic substitution. Given enough energy, any gas can be excited into the plasma state of matter. There are many temperature and pressure conditions where this phenomenon will occur, but for practical considerations, radio frequency or microwave energy is commonly used, enabling these processes to take place at low temperatures (about 25-100° C.) and low pressure (about 0.1 to 1.0 Torr), where surface reactions are feasible without bulk interactions. Even with benign gases, such as oxygen or nitrogen, plasma surface treatment can create highly reactive species at low temperatures. High energy ultraviolet light is emitted in the process, which along with the high energy ions and electrons, provides the energy necessary to fracture polymer bonds and initiate chemical reactions on a material's surface. Only a few atomic layers on the surface are usually involved in the process, so the bulk properties of the material remain unaltered by the chemistry, while the low process temperature eliminates concerns about thermal modification or distortion of the bulk of the material.

Plasma surface treatment may be performed with a low pressure, gaseous glow-discharge process that has been used in the aerospace, semiconductor, and electronics industries for cleaning, etching, and surface treatment of various materials. Plasma surface treatment does not affect the interior portion of the material and plasma treated parts are generally visually and physically indistinguishable from untreated parts. Plasma species are chemically active and/or can physically modify the surface of materials and may therefore serve as the basis for reacting and/or polymerizing chemical compounds and may also be used to modify existing compounds. Glow discharge and arc discharge produce a class of plasmas described as current-maintained plasmas, since they are maintained by the passage of current therethrough. Such plasmas conduct only because current is passed therethrough and the conductivity falls off quickly if the source of energy to the charge carriers is removed.

Plastics, polymers, and resins are widely accepted materials that are used for many in vivo and in vitro medical applications. Many of these materials have properties that lend themselves well to the manufacture of medical appliances or devices in that they are relatively inexpensive and easily molded or formed into complex shapes, and have bulk physical properties that may be selected from a wide range of parameters such as rigidity and temperature stability. Fabrication procedures that require bonding of inert materials, such as fluoropolymers, are difficult to achieve, and biological interface reactions within the body or in the laboratory can limit their in vivo and in vitro performance unless adhesive capacity of the material is improved.

Atmospheric plasma surface treatment according to the present methods eases these limitations by modifying the surfaces of inert materials, including fluoropolymers. In some cases, the deposition of plasma-etched material, volatilized from a polyurethane fixture for example, alters just the first few atomic layers of the inert substrate, which consequently renders the surface of most medical polymers wettable so that adhesive bonding can be achieved with inert materials such as polyolefins, silicones, and fluoropolymers. The surface of the inert material may thereby be modified without loss of the desirable characteristics of the bulk of the material.

Plasma surface treatment can promote unique reactions by appropriate choice of reactant gases and unusual polymer byproducts and structures can be formed. In many instances, plasma surface treatment uses gases such as oxygen or nitrogen to provide adequate surface activation for enhanced wetting and adhesive bonding. With other targeted end results or substrate materials, it may be necessary to utilize reactants which result in grafting reactions, or plasma surface treatment chemistry modification, in order to achieve the desired results. Materials that form volatile byproducts upon reaction with the plasma can be used to redeposit material and reaction products thereof onto the inert substrate. For example, using a dielectric fixture made of polyurethane allows the plasma to etch the polyurethane and form volatile byproducts. These byproducts then deposit and/or react with the inert substrate to treat the surface of the inert substrate. At the same time, the surface of the inert substrate may be etched and/or chemically activated by the plasma, such that the volatile byproducts formed from etching of the polyurethane fixture more readily deposit and/or chemically react with the surface of the inert substrate. Thus, the inert substrate surface does not require physical or chemical preparation prior to deposition of the volatile byproducts.

In forming plasma, oxidizing species such as air, oxygen, water vapor, or nitrous oxide may be used to remove/etch material such as organics, leaving functional oxygen-containing groups on the surface. These functional oxygen-containing groups greatly enhance wetting, improve adhesive bonding, and in some instances, may create charged surfaces. Plasma surface treatment with reducing gas species such as hydrogen or methane, often diluted with argon, helium, or nitrogen, may also be used to remove organics from surfaces that are sensitive to oxidation. This chemistry may also be used to partially substitute hydrogen atoms for fluorine or oxygen on polymer surfaces. The noble gas species, such as argon or helium, are chemically inert, so they do not combine or become part of the surface chemistry. Instead, they transport energy to break chemical bonds in polymer chains. Broken polymer chains can then recombine with other reactive sites, resulting in significant molecular restructuring and/or cross-linking; for example, these chemical grafting reactions include formation of reaction products with volatile material etched from the polyurethane reaction chamber.

Plasma surface treatment may also include polymerization and deposition processes that utilize a wide variety of gases, including organic or organo-metallic compounds, which may be used to deposit nonvolatile polymer films. In many instances, these reactant gases are toxic, corrosive, or otherwise hazardous and require special handling such as heated gas transfer plumbing and measurement instrumentation, reactor exhaust scrubbing, and trapping of reaction byproducts. Polymerization processes generally necessitate frequent cleaning of the reaction chamber, since all surfaces exposed to the plasma will be coated.

Plasma surface treatment may be performed using a system that includes the following: (1) an electric power source for the initiation and maintenance of plasma (e.g., by glow discharge) having two electrodes, (2) a dielectric comprising a polymer such as polyurethane, and (3) a control system for gas flow. Examples of systems that may be adapted for use with the present methods include those described in U.S. Pat. No. 5,798,146 to Murokh et al., which is incorporated herein by reference. Manufacturers of plasma systems that may be adapted for use in the present methods include the following: 3DT LLC (Germantown, Wis.); Enercon Industries (Menomonee Falls, Wis.); Plasmatreat North America, Inc. (Mississauga, ON, Canada); PVA TePla America, Inc. (Corona, Calif.); Tantec EST Inc. (Glendale Heights, Ill.); and Tri-Star Technologies (El Segundo, Calif.). In some embodiments, these systems may further include an optional pump or vacuum system. The pump or vacuum is not used to generate a true vacuum plasma, but instead may be used in some aspects to draw gas or vaporized material into the atmospheric plasma. In some further aspects, the pump or vacuum may be used to reduce the atmospheric pressure in order to increase volatilization of materials or products fed into and/or produced within the atmospheric plasma reaction chamber.

Atmospheric plasma surface treatment includes dielectric-barrier discharge methods. Features of dielectric-barrier discharge used in the present disclosure are found in Kogelschatz, "Dielectric-barrier Discharges: Their History, Discharge Physics, and Industrial Applications," *Plasma Chemistry and Plasma Processing*, Vol. 23, No. 1 (March 2003), which is incorporated herein by reference. Atmospheric plasma systems generally work in an open environment at atmospheric pressure and include a power supply and one or more pairs of electrodes. The electrodes may be contained within a reaction chamber that includes a dielectric fixture having at least a portion made of a polymer such as polyurethane. The main principal of these systems is to create an electrical discharge to contact and modify a substrate surface by a process described as plasma surface interaction (PSI).

The plasma effect on the substrate strongly depends on the exposure time. In other words, each particular substrate requires some minimum exposure time necessary to activate its surface. The required level of surface modification depends on the application (e.g., printing, bonding, coating, etc.) as well as on properties of the applied ink, adhesives, coatings, and curing process. Very little overlap between necessary exposure and thermally safe substrate handling can reduce the applicability. Particular problems exist with inert substrates where the surface gets burned rather than modified. This may also be the case for heat sensitive materials, thin wall plastic objects, wires with thin insulation, fiberoptics, thin coating layers, etc. The problem may be partly solved, for example, by using multiple, shorter treatments.

The present systems and methods include in-line plasma treatment of inert substrates. An example of a suitable apparatus is the PT-1000 atmospheric plasma treatment system by Tri-Star Technologies (El Segundo, Calif.). This system is based on the Dielectric Barrier Glow Discharge phenomenon.

Dielectric barrier discharge is a phenomenon used in industrial processes such as ozone generation, electret production, corona web treatment, etc. Plasma generation takes place in a gap between two electrodes, where a dielectric material may be proximal to one electrode. The substrate to be treated may be located between the electrodes.

Referring now to FIG. 1, an embodiment of a dielectric barrier discharge system 100 is shown. The system 100 includes two electrodes 110 comprising electrically conductive material spaced to form a discharge gap 120. A substrate 140 to be treated is disposed between the electrodes 110 within the discharge gap 120, where the substrate 140 may include any of the inert substrates as described. A liquid dielectric material 130 within a reservoir 150 is located proximal to one electrode 110. As shown, the reservoir 150 is open and may be in the form of a pan or dish placed atop the electrode 110. The liquid dielectric material 130 is retained by the reservoir 150, but may vary in viscosity from a highly viscous or even gel-like state to a solution having very low viscosity and a watery state. For example, the liquid dielectric material 130 may include a polymer such as polyurethane.

Plasma is generated by establishing an electrical potential between the electrodes 110 that forms discharges originating from the liquid dielectric material 130. For example, dielectric barrier discharge may produce a field of microdischarges across the surface of the liquid dielectric material 130. Plasma forms at and/or near the surface of the liquid dielectric material 130 and may extend towards the substrate 140 and the opposite electrode 110, across the discharge gap 120. Plasma-etched products from the liquid dielectric material 130 (e.g., etched polyurethane residues) deposit onto the surface of the substrate 140. The plasma may also react with and modify the surface of the substrate 140.

The electrodes 110 and the reservoir 150 holding the liquid dielectric material 130 are typically planar in shape, but may take other forms to accommodate different substrate 140 geometries. For example, the reservoir 150 may be curved and covered with a liquid dielectric material 130 having a thick gel-like consistency that does not readily flow or settle. The electrodes 110 and the dielectric material 130 may be in fixed relation to each other and may be static relative to the substrate 140 or vice versa. For example, where the substrate 140 is larger than the electrodes 110, only a portion of the substrate may be treated at any given time. In this case, the substrate 140 may be passed between the electrodes 110 at a constant rate to uniformly treat a respective portion of the substrate 140. Alternatively, the rate the substrate 140 may be moved or the generation of plasma may be varied to provide discontinuous treatment. In addition, substrate 140 may be rotated so that more than one portion, side, or face of the substrate 140, or the entire surface of the substrate 140, is oriented toward the dielectric material 130 and plasma for similar or different times. For example, a medical implant electrical lead having a Teflon® coating, where the lead may be longer than the electrodes 110, can be passed through the discharge gap 120 between the electrodes while the lead is simultaneously rotated. In this manner, at least a portion of the Telfon® coating along the lead length may be uniformly plasma treated. Plasma treatment and exposure time may be dependent on the length of the electrodes 110 and dielectric material 130 and the feed rate of the substrate 140 there through.

In some embodiments (not shown), the proximal electrode 110 to the liquid dielectric material 130 may be configured to function as the reservoir 150. In some embodiments, the reservoir 150 may be formed of a dielectric material that is similar to or different than the liquid dielectric material 130. For example, the reservoir 150 may be formed of a solid polymer such as polyurethane while the liquid dielectric material 130 comprises a polyurethane solution.

In some embodiments, the reservoir 150 may include a temperature control element (not shown) operable to raise or lower the temperature of the liquid dielectric material 130. For example, vapor pressure of one or more components of the liquid dielectric material 130 may be altered by changing the temperature. When the temperature is increased, one or more components of the liquid dielectric material 130 may more readily volatilize and/or react with plasma discharges generated within or at the dielectric surface. Alternatively, the liquid dielectric material 130 may be cooled to attenuate the vapor pressure and/or reaction rate between one or more components and the plasma.

One or more components of the liquid dielectric material 130, or the solution as a whole, may be consumed during the plasma treatment. In this case, the liquid dielectric material 130 may be replaced in whole or in part, replenished by addition of fresh solution, or recharged by continuously or periodically circulating the liquid dielectric material 130 between the reservoir 150 and a holding tank (not shown).

In some embodiments, the dielectric barrier discharge system includes a vacuum or pump system (not shown) operable to reduce the pressure to below atmospheric pressure and/or to purge or exchange the atmosphere within the dielectric barrier discharge system. For example, vacuum may be used to reduce the pressure below atmospheric pressure, thereby increasing vapor pressure of one or more components of the liquid dielectric material 130. The vacuum or pump system may be used to replace the atmosphere (e.g., air) within the dielectric barrier discharge system with an inert gas, such as argon or helium. Other materials such as aerosolized materials, organic gases, and monomers may also be fed into the dielectric barrier discharge system using the vacuum or pump system. For example, monomers fed into the system may be activated by the plasma and co-react and/or co-deposit with plasma-etched material from the dielectric material to modify the substrate 140 surface.

Dielectric barrier controlled discharge includes a large number of transient microdischarges that are distributed statistically on the treated surface. The microdischarges in dielectric barrier controlled discharge include four phases:

1. Townsend Phase. The number of charged particles (electrons and ions) increases exponentially without disturbing the applied electrical field.

2. Streamer Phase. The formation of the conducting channel inside the gas gap.

3. Cathode Sheath Phase. The current reaches its maximum value.

4. Quenching Phase. The electrical charge accumulated on the dielectric surface reduces the electrical field in the gap below breakdown threshold and prevents formation of the new ion-electron pairs in the gas. On the other hand, the retaining charge increases the electrical field across the surface and causes the local surface microdischarge.

The complete discharge development has a duration of several nanoseconds. Electrons are the predominant carriers of the current. The plasma forms randomly distributed filaments of about 100 micron diameter with about 1.5 mm footprints on the dielectric material's surface. Due to the short period of the discharge, there is no significant heating of the gas within the gap and the substrate. Depending on the parameters of the applied high voltage signal (frequency, duty cycle, waveform, etc.), the filaments tend to appear at the same places leading to the non-uniform treatment. The charged spots remaining on the surface from the previous micro-breakdowns are preferential points for the initiation of a new microdischarge with the opposite polarity.

To cover the entire surface with microdischarges (homogeneous treatment), a combination of high voltage periods with no voltage periods is used (~1 msec trains of ~20 msec HV pulses in a ~1 sec interval). The gap between electrodes may be filled with different gases or gas mixtures depending on the required plasma properties and expected surface transformation. The interaction of the microdischarges generated at near atmospheric pressure with the dielectric material's surface is similar to plasma-surface interaction at low pressure.

In the former case, however, interaction is localized at the footprints of the discharges and seems to occur at much faster rate. It could be assumed that surface modification under the discharge footprint reaches a saturation level during one cycle. Since footprints are randomly distributed over the surface, increase of the exposure time provides more uniform coverage of the surface with discharges rather than changes an intensity of the surface modification.

Air at atmospheric pressure is the most practical gas for industrial application of in-line plasma treatment. However, other gas mixtures could be blown through the plasma chamber at a slightly excessive pressure if required. Comparison of air and helium dielectric barrier glow discharges at atmospheric pressure for polypropylene surface treatment shows that air discharge has a clearly filamentary structure. Several pulses of nanosecond microdischarges occur during each half cycle at the applied voltage about 10 kV rms. The overall discharge duration may be about 5 msec that may be much less than a cycle period. An increase in the frequency of the applied voltage leads to more rapid surface treatment.

When the gap between electrodes is filled with helium at atmospheric pressure, the discharge changes from filamentary to homogeneous and covers the entire surface. The discharge duration in helium during a half cycle period may be comparable to the one in air, but the current amplitude may be much lower. The duration could be easily estimated assuming that plasma quenching is due to the dielectric charging. Local charge densities in the vicinity of the polymer surface for helium and air plasma are about $4 \times 10^{10}$ and $10^{13}$ charges/cm$^2$ pulse, respectively. The charge Q accumulated in t seconds on the dielectric surface for the current i will be Q=i×t. That gives t ~6.4 msec at the average current density in order of 1 mA/cm$^2$ for the discharge in helium. The charge density for the air filamentary discharge may be obtained based on metallic "point to plane" discharge data. The discharge duration about 100 nsec gives current density of 16 A/cm$^2$. This current would be typical rather for an arc discharge than for the dielectric barrier discharge. A "uniform plane to plane" discharge would have lower current density. It can be difficult to distinguish a real plasma current from the total current in the systems like these, due to significant impedance effects at high frequencies.

Atmospheric plasma treatment, for example employing the PT-1000 Plasma Treatment System, improves the wettability characteristics of the treated material. This may be accomplished by forming a plasma curtain that surrounds the substrate to be treated, such as a wire, cylinder, or length of tubing. The surface may be bombarded with charged particles and high energy UV photons. A solid state programmable generator produces a high voltage high frequency signal that may be applied to the electrode proximal to a dielectric material.

In most cases, the plasma produces a blue color glow that can be observed within the discharge gap. The intensity of the plasma treatment may be defined as the amount of energy transmitted to the unit area of the substrate surface per unit of time, and may be dependent on the voltage and frequency of the driving signal. The level of the plasma treatment at a given intensity may be proportional to the exposure time (length of an electrode divided by the line speed for an in-line system) and inversely related to the size of the substrate surface. The time dependence is usually exponential, with saturation occurring after a long period of exposure (e.g., 10 sec or more) and linear for short periods of time (e.g., 0.1 sec or less). To obtain the same quality of treatment for larger substrate surface areas or to achieve higher throughput speeds, the plasma intensity must be increased. Adjusting the electrode voltage (e.g., from 1 to 15 kV) can change this intensity. Despite the high potential applied to the electrode, the active currents inside the chamber are extremely low. At normal operating conditions, the average power consumption for the system may be only about 100 W. The threshold conditions as well as the plasma density and composition (concentration of specific ions and electrons) depend on the pressure and nature of gas in the dielectric chamber, substrate surface area, dielectric constant, material properties, etc.

The present systems and methods may employ dielectric materials comprising polymeric fixtures, including fixtures made of polyurethane, which are etched by the plasma during the treatment process and the resulting volatilized material may be deposited onto the inert substrate surface. At least a portion of the dielectric material may be made of a polymer such as polyurethane.

Dielectric materials including polyurethane may be formed from aliphatic, cycloaliphatic, aromatic, and polycyclic polyurethanes. These polyurethanes typically are produced by reaction of a polyfunctional isocyanate with a polyol, often in the presence of a catalyst, according to established reaction mechanisms. Useful diisocyanates for employment in the production of a polyurethane include, for example, dicyclohexylmethane-4,4'-diisocyanate, isophorone diisocyanate, 1,6-hexamethylene diisocyanate, cyclohexyl diisocyanate, and diphenylmethane diisocyanate. Combinations of one or more polyfunctional isocyanates may also be used. Useful polyols include polypentyleneadipate glycol, polytetramethylene ether glycol, polyethylene glycol, polycaprolactone diol, poly-1,2-butylene oxide glycol, and combinations thereof. Chain extenders such butanediol or hexanediol may also optionally be used in the reaction. Many useful types of polyurethanes also are commercially available and include: PN-04 or PN-09 from Morton International, Inc., (Seabrook, N.H.), and X-4107 from B.F. Goodrich Company, (Cleveland, Ohio). These polyurethanes may be used to form solid dielectric materials or may be used in solution with one or more organic and/or aqueous solvents to form a liquid dielectric material. In addition, various polyurethanes can be dissolved in certain solvents, and certain polyurethane grades exist that are specifically for use in solution casting or for coating.

Examples of suitable polyurethanes include Tecothane® from Lubrizol Corporation (Wickliffe, Ohio) and Elasthane™ from DSM Biomedical, Polymer Technology Group (Berkeley, Calif.). Tecothane® polyurethanes include a family of aromatic, polyether-based TPUs that have a range of durometers that are formulated and manufactured for medical applications. Elasthane™ thermoplastic polyether urethane (TPU) is a high strength, aromatic biomedical polymer. Elasthane™ TPUs have high molecular weights and low solvent extractables. Elasthane™ is formed by the reaction of polytetramethyleneoxide and an aromatic diisocyanate and a low molecular weight glycol chain extender.

The dielectric barrier discharge system may include a control system having the following features. The control system may operate a vacuum or pump system to control gas within the dielectric barrier discharge system. Gas flow rate through the plasma reaction chamber is one of the factors that may affect the plasma surface treatment, and may be used to introduce additional reactive species, such as monomers, which may be deposited onto the substrate surface in addition to volatilized polyurethane material etched from the reaction chamber. For example, gas flow containing one or more compounds (e.g., monomers) may be introduced into the plasma within the reaction chamber to provide additional reactive species, which may react with the volatilized polyurethane material and/or react with each other on the inert substrate surface being modified. For example, plasma deposition may be used to introduce volatilized monomer(s) and polymerize a layer of polymer on the inert substrate surface, along with deposition and/or reaction with the etched and volatilized polyurethane byproducts. Changes in gas flow rate during the process are usually avoided to ensure uniformity in reaction and deposition. Gas flow may be carefully controlled using a metering needle valve or a mass-flow controller.

The present systems and methods are used to modify the surface of substrates including inert substrates to provide better adhesive capacity to other materials. Particularly important inert substrates include fluoropolymers. Fluoropolymers can be broadly categorized into two basic structural classes. The first class includes thermoplastic and elastomeric fluorinated polymers, homopolymers, copolymers, terpolymers, etc, comprising interpolymerized units derived from vinylidene fluoride (sometimes referred to as "$VF_2$" or "VDF"). Fluoropolymer materials of this first class may comprise at least 3% by weight of interpolymerized units derived from $VF_2$. Such polymers may be homopolymers of $VF_2$ or terpolymers and copolymers of $VF_2$ and other ethylenically unsaturated monomers.

$VF_2$-containing polymers and copolymers can be made by conventional means, for example by free-radical polymerization of $VF_2$ with or without other ethylenically-unsaturated monomers. The preparation of colloidal aqueous dispersions of such polymers and copolymers is described, for example, in U.S. Pat. No. 4,335,238. In some embodiments, fluorinated olefins may be copolymerized in colloidal aqueous dispersions, carried out in the presence of water-soluble initiators that produce free radicals, such as, for example, ammonium or alkali metal persulfates or alkali metal permanganates, and in the presence of emulsifiers, such as, in particular, the ammonium or alkali metal salts of perfluorooctanoic acid.

Useful fluorine-containing monomers include hexafluoropropylene ("HFP"), tetrafluoroethylene ("TFE"), chlorotrifluoroethylene ("CTFE"), 2-chloropentafluoro-propene, perfluoroalkyl vinyl ethers, e.g. $CF_3OCF\!=\!CF_2$ or $CF_3CF_2OCF\!=\!CF_2$, 1-hydropentafluoropropene, 2-hydro-pentafluoropropene, dichlorodifluoroethylene, trifluoroethylene, 1,1-dichlorofluoroethylene, vinyl fluoride, and perfluoro-1,3-dioxoles such as those described in U.S. Pat. No. 4,558,142 (Holland et al.). Certain fluorine-containing di-olefins also are useful, such as perfluorodiallylether and perfluoro-1,3-butadiene. Said fluorine-containing monomer or monomers also may be copolymerized with fluorine-free terminally unsaturated olefinic comonomers, e.g., ethylene or propylene. Preferably at least 50% by weight of all monomers in a polymerizable mixture are fluorine-containing. Said fluorine-containing monomer may also be copolymerized with iodine- or bromine-containing cure-site monomers in order to prepare peroxide curable polymer. Suitable cure-site monomers include terminally unsaturated monoolefins of 2 to 4 carbon atoms such as bromodifluoroethylene, bromotrifluoroethylene, iodotrifluoroethylene, and 4-bromo-3,3,4,4-tetrafluorobutene-1.

Commercially available fluoropolymer materials of this first class include, for example, THV 200 fluoropolymer (available from Dyneon LLC of Saint Paul, Minn.), THV 500 fluoropolymer (also available from Dyneon LLC), Kynar™ 740 fluoropolymer (available from Elf Atochem North America, Inc.), Fluorel™ FC-2178 fluoropolymer (available from Dyneon LLC), and those fluoropolymers sold under the "Viton" tradename by DuPont.

The second class of fluorinated material comprises those thermoplastic and elastomeric fluorinated polymers, copolymers, terpolymers, etc, comprising interpolymerized units derived from one or more of hexafluoropropylene ("HFP") monomers, tetrafluoroethylene ("TFE") monomers, chlorotrifluoroethylene monomers, and/or other perhalogenated monomers and further derived from one or more hydrogen-containing and/or non-fluorinated olefinically unsaturated monomers. Useful olefinically unsaturated monomers include alkylene monomers such as ethylene, propylene, 1-hydropentafluoropropene, 2-hydropentafluoropropene, vinylidene fluoride, etc.

Fluoropolymers of this second class can be prepared by methods described in the fluoropolymer art. Such methods include, for example, free-radical polymerization of hexafluoropropylene and/or tetrafluoroethylene monomers with non-fluorinated ethylenically-unsaturated monomers. In general, the desired olefinic monomers can be copolymerized in an aqueous colloidal dispersion in the presence of water-soluble initiators which produce free radicals such as ammonium or alkali metal persulfates or alkali metal permanganates, and in the presence of emulsifiers such as the ammonium or alkali metal salts of perfluorooctanoic acid. See for example U.S. Pat. No. 4,335,238.

Representative of the fluoropolymer materials of the second class are poly(ethylene-co-tetrafluoroethylene) (ETFE), poly(tetrafluoroethylene-co-propylene), poly(chlorotrifluoroethylene-co-ethylene) (ECTFE), and the terpolymer poly(ethylene-co-tetrafluoroethylene-co-hexafluoropropylene), among others; all of which may be prepared by the above-described polymerization methods. Many useful fluoropolymer materials also are available commercially, for example from Dyneon LLC under the trade designations Hostaflon™ X6810, and X6820; from Daikin America, Inc. (Carrollton, Tex.), under the trade designations Neoflon™ EP-541, EP-521, and EP-610; from Asahi Glass Co. (Tokyo, Japan) under the trade designations Aflon™ COP C55A, C55AX, C88A; and from DuPont (Wilmington, Del.) under the trade designations Tefzel™ 230 and 290.

In some embodiments, useful fluoropolymer materials include those from Asahi Glass Co. (ACG Chemicals Americas, Inc., Exton, Pa.), including Fluon® fluoropolymer resins and compounds, including ethylene/tetrafluoroethylene (ETFE), modified ETFE, and poly(tetrafluoroethylene) (PTFE); Lumiflon® fluoropolymer coatings; and Aflas® fluoroelastomer, an alternating copolymer of tetrafluoroethylene and propylene.

The above-described fluoropolymers may be blended with one another or blended with another fluorinated or non-fluorinated polymer to form a composite material useful to construct an inert substrate. Polyvinylidene fluoride, for example, may be blended with polymethylmethacrylate. The described fluoropolymers may also be dehydrofluorinated according to the method described in WO 98/08879.

The present systems and methods may be used to improve adhesion between a fluoropolymer that may be part of a medical device and another portion of the same or different medical device. Suitable adhesion between a fluoropolymer coating and the medical device and/or adhesion between another material placed over the fluoropolymer may be important for construction and/or proper functioning of the device.

Examples of medical devices that can benefit by including a fluoropolymer that is surface treated according to the present systems and methods include, but are not limited to: a wire, a guidewire, a tube, a catheter, a cannula, a scope (e.g., rigid or flexible endoscope, laparoscope, sigmoidoscope, cystoscope, etc.) a probe, an apparatus for collecting information from a location within the body (e.g., an electrode, sensor, camera, scope, sample withdrawal apparatus, biopsy or tissue sampling device, etc.). A portion of the medical device may be made from a radiopaque, biocompatible metal such as platinum, gold, tungsten, nitinol, elgiloy, stainless steel, or tantalum, and/or may be made of a polymer impregnated or otherwise modified to be visible under x-rays by various means described in the art. Alternatively, the medical device's outer surface may be made of a plastic or polymer material which, in at least some embodiments, may be visualized using ultrasound, magnetic resonance imaging, radiographic imaging, or other medical visualization methods described in the art.

The inert substrate may comprise a material that is lubricious or has a low coefficient of friction, such as polytetrafluoroethylene (e.g., Teflon®). The inert substrate may be formed about the outer surface of the medical device in a non-continuous manner (e.g., in discrete ridges, bumps or areas) or form a polymer coating disposed as a generally smooth continuous polymer coating surface. In some embodiments, the inert substrate may be a radioopaque composite.

Where the medical device including an inert substrate is an implantable lead, for example, and particularly in the context of an implantable cardiac lead, there is often a need to remove the lead after it has been implanted in a patient's body for some period of time. In conjunction with lead removal, it is often necessary to apply traction to the lead, in order to pull it free from tissue adhering thereto. It is therefore beneficial to have reinforcement of some type extending along the lead body in order to prevent breakage, separation, or partial disassembly of the lead during removal and to ensure that different materials and/or portions of the lead remain affixed and do not separate.

In the context of implantable cardiac leads, cabled or stranded conductors can be used in place of coiled conductors. These cabled or stranded conductors, such as disclosed in U.S. Pat. No. 5,584,873 issued to Shoberg et al., U.S. Pat. No. 5,760,341 issued to Laske et al. and U.S. Pat. No. 5,246,014 issued to Williams et al., provide an increased tensile strength lead, at least along the segment between the point at which the stranded or cabled conductor is coupled to an electrode and the point at which the conductor is coupled to an electrical connector at the proximal end of the lead. While these conductors provide enhanced tensile strength, in most transvenous cardiac pacing leads employing cabled or stranded conductors, the conductor which extends to the distal-most portion of the lead may still be a coiled conductor in order to permit passage of a stylet. This distal-most portion of the lead, particularly in the context of leads employing tines or other passive fixation mechanisms, is the portion of the lead to be most likely to be firmly embedded in fibrous tissue. This portion of the lead in particular should be capable of withstanding high tensile forces without breakage or separation of lead components.

The present systems and methods reduce problems associated with extraction of such leads and other medical devices post-implantation by increasing adhesion between one or more fluoropolymer components and one or more other materials of the lead or device. The present methods provide a lead or device which may be easier to extract and less likely to be damaged or have one or more portions separate during the extraction process. An insulative coating or tubing, which comprises an inert substrate like a fluoropolymer, used to cover strand and/or coiled conductors employed in the lead, are made to have increased adhesiveness where they contact other portions/materials of the lead or device. The fluoropolymer coating or tubing may be treated to enhance bonding performance, so that the coating or tubing, for example, may be usefully adhered to molded or extruded plastic components or other materials at either end of the lead, providing for a mechanism for transmission of tensile force along the lead body.

In the context of a lead having a fluoropolymer coating, a conductor coupled to the tip electrode may be a coiled conductor surrounded by a heat shrink tube of fluoropolymer (e.g., polytetrafloroethelene (PTFE)) which has been treated according to the present methods. The distal end of the heat shrink tube may be bonded to one or more of the tine sleeve, the ring-coil spacer component and the tip-ring spacer component and to the connector assembly at the proximal end of the lead. The heat shrink PTFE tubing, in conjunction with the associated coiled conductor and the adhesive bonds at the proximal and distal end of the lead, provides a mechanism for enhanced tensile strength extending along the entire length of the lead. The cabled conductor coupled to the ring electrode referred to above may correspondingly be provided with a plastic insulative coating, also treated to improve adhesion.

For example, the cabled conductor may be provided with a coating of ethylene tetrafluoroethylene (ETFE), modified by plasma surface treatment using a polyurethane dielectric material in order to provide for increased bonding capabilities. The insulative coating on the cabled conductor may likewise be bonded to plastic components or components made from other materials located at the proximal and distal ends of the lead, in turn allowing for distribution of tensile forces between the mechanical joints coupling the cabled conductor to the metal electrode and electrical connector components located at the distal and proximal ends of the leads, respectively, and adhesive bonds between the insulation and associated nearby plastic parts. The insulation may, for example, be bonded to the molded parts associated with the tip-ring spacer and the connector assembly and/or to the extruded plastic tubing making up the lead body. By this mechanism, the ability of the cabled conductors to transmit tensile forces from the proximal end of the lead to the distal portion of the lead without damage to the lead may be further enhanced. The improved adhesiveness and bonding characteristics provided by surface treatment of the insulative coatings and/or tubes also assist in maintaining effective seals against fluid intrusion and migration within the lead body.

The present systems and methods may also be used for treating the surface of other instruments and apparatuses. For example, the present systems and methods may be used for controlling the wettability of test tubes and lab vessels, for pre-bonding preparation of angioplasty balloons and catheters, for treating blood filtration membranes, and to manipulate surface conditions of in vitro structures to enhance or inhibit cell growth.

Plasma surface treatment of inert substrates like fluoropolymers may enhance wetting of the substrate. One technique used to evaluate plasma surface treatment is a wetting angle test using a contact goniometer. Surface roughness and substrate cleanliness need to be tightly controlled to obtain quantitative data. Standard wetting solutions are used to obtain accurate surface energy values. Most untreated polymer substrates are only poorly wettable, where initial contact angles may vary from 60-100 degrees. Low contact angles, as low as about 20 degrees, may be achieved after plasma exposure using the present systems and methods. When these substrates are properly packaged after treatment, the contact angle can be stable for several years.

Plasma surface treatment may remove organic residues from the substrate surface and may chemically react gas, such as air including oxygen, with the surface to form covalent carbon-oxygen bonds, which are more polar and more reactive than carbon-hydrogen bonds. The increased polarity of the surface accounts for substantial increases in wettability and adds a degree of covalent bonding to the surface-adhesive interface. Other gases may be used to attain similar results in instances where oxidizing species may be harmful to components of the assembly.

Many intravascular devices, such as balloon catheters, are assembled by adhesive bonding of one or more polymeric components, including components formed from inert substrates like fluoropolymers. Chemical surface activation or mechanical surface roughening techniques provide only modest bonding performance, with bond failures noted after just a few repetitive inflations of the balloon catheter. With plasma treatment, substantially more repetitions are achievable without separation of the materials.

Bond strength realized between the surface-treated inert substrate and another material, including instances where an adhesive may be used to facilitate bonding, may be affected by initial cleanliness of the surface, wetting of the surface by the adhesive, cross-linking effects, and chemical interaction of the adhesive with the deposited and coated surface. Any mold release compounds, unpolymerized monomers, plasticizers, or additives that may have migrated to the surface of the inert substrate should be removed by cleaning or washing before surface modification is attempted. In some cases, immediate bonding and assembly after plasma-treatment can prevent contamination and/or subsequent reactions that may degrade the enhanced adhesiveness provided by the plasma treatment and deposition of etched urethane byproducts. Once the surface has been plasma treated and bonded, in some instances, the affixed layers are permanently bonded.

In some embodiments, the present methods and materials produced by these methods are used to increase bonding of anti-thromobotic materials to inert substrates. For example, to increase biocompatibility in vivo, the issue of thrombogenesis (the propensity of a surface to form or initiate clotting) should be addressed. Many unmodified materials encourage protein binding to the material's surface and thus initiate the process of clot formation. To combat this process, antithrombotic (anticlotting) coatings are often applied to the surface of a medical device, but when dealing with polymers these antithrombotic coatings often fail to effectively bond to the polymer surface. The present plasma surface treatment improves adhesion of antithrombotic compounds or materials, which now achieve effective chemical bonding to the previously inert material surfaces. Process variables are dependent upon a range of factors including selection of the base materials, composition of the antithrombotic, and the expected product lifetime. For example, plasma surface treatment according to the present methods of a fluoropolymer coated catheter and subsequent bonding of heparin to coat the fluoropolymer surface of the catheter may prevent protein attachment after a 30-day indwelling. As another example, plasma modified blood filters show a substantial reduction in platelet retention compared to untreated materials.

In some embodiments, the substrate treated according to the present methods may be first overlaid with a mask so that only one or more portions of the substrate receive a plasma deposition coating or film. The mask may be removed following the deposition process. In this way, an inert substrate may have a portion that has increased adhesiveness, provided by the plasma deposited coating or film, and a portion that retains the original inert substrate surface. The treated surface may then be bonded to another material in manufacture of a medical device, for example, while the nonstick and/or lubricious properties of the untreated portion may contact tissue or body fluids.

In some embodiments, a portion of the surface of the inert substrate treated according to the present methods may be milled or abraded following plasma deposition of the coating or film in order to remove the coating or film and expose untreated substrate. In this way, the treated portion has increased adhesiveness and the milled or abraded portion exposes inert substrate material having practically similar or the same surface properties as the surface of untreated inert substrate.

The present technology provides several benefits and advantages. The present systems and methods improve adhesiveness of the surface of an inert substrate (e.g., fluoropolymer), which improves bonding between the inert substrate and another surface. The surface of the inert substrate may be plasma treated using a dielectric material having at least a polymeric portion (e.g., polyurethane), where the reaction chamber material may be etched by the plasma and the volatile byproducts are deposited onto the surface of the substrate. For bonding, the other material may be another type of material entirely, such as a metallic or ceramic substrate, or may be another polymer or inert substrate, or may be the same or a different inert substrate that may also be treated according to the present methods. The present systems and methods do not destructively treat the inert substrate. Multi-layered articles may be produced where the present systems and methods are employed to increase adhesion between two or more of the layers. The action of adhesives, including tie layers, for adhering the inert substrate to another surface may also be improved. Furthermore, the present systems and methods minimize and/or avoid hazardous chemicals, for example those used to chemically etch a substrate surface, and the present methods may be effectively used on irregularly shaped surfaces that may be difficult to physically modify by abrasion, for example.

The embodiments and the examples described herein are exemplary and not intended to be limiting in describing the full scope of apparatus, systems, and methods of the present technology. Equivalent changes, modifications and variations of some embodiments, materials, compositions and methods can be made within the scope of the present technology, with substantially similar results.

What is claimed is:

1. A method of increasing adhesiveness of an inert substrate comprising:
    locating a reservoir of a liquid dielectric material adjacent to an electrode within a plasma reaction chamber of a dielectric barrier discharge system, the electrode being one of a pair of electrodes spaced apart from one another to form a discharge gap, and at least a portion of the liquid dielectric material comprising a polymer;
    disposing the inert substrate between the pair of electrodes within the discharge gap; and
    establishing an electric potential between the pair of electrodes to produce a field of microdischarges across a surface of the liquid dielectric material, and to form a plasma that deposits resulting volatile byproducts of the liquid dielectric material onto at least a portion of a surface of the inert substrate.

2. The method of claim 1, wherein the polymer comprises a polyurethane.

3. The method of claim 1, wherein the plasma reaction chamber is at atmospheric pressure when the plasma is formed.

4. The method of claim 1, wherein the inert substrate comprises a fluoropolymer.

5. The method of claim 1, further comprising heating or cooling the liquid dielectric material.

6. The method of claim 1, further comprising replacing an atmosphere in the plasma reaction chamber with an inert gas prior to establishing the electric potential.

7. The method of claim 1, further comprising masking a portion of the surface of the inert substrate prior to establishing the electric potential.

8. A method of treating a surface of an inert substrate for inclusion in a medical device, the method comprising:
    locating a reservoir of a liquid dielectric material adjacent to an electrode within a plasma reaction chamber of a dielectric barrier discharge system, the electrode being one of a pair of electrodes spaced apart from one another to form a discharge gap, and at least a portion of the liquid dielectric material comprising a polymer;
    disposing the inert substrate between the pair of electrodes within the discharge gap;
    establishing an electric potential between the pair of electrodes to produce a field of microdischarges across a surface of the liquid dielectric material, and to form a plasma that deposits resulting volatile byproducts of the liquid dielectric material onto a surface of the inert substrate; and
    removing the deposited volatile byproducts from a portion of the surface of the inert substrate.

9. The method of claim 8, wherein removing the deposited volatile byproducts from the portion of the surface of the inert substrate comprises abrading or milling the surface of the inert substrate.

10. The method of claim 1, wherein the inert substrate comprises at least a portion of a medical device.

11. The method of claim 8, wherein the medical device comprises a cardiac lead.

12. The method of claim 8, wherein the polymer comprises a polyurethane.

13. The method of claim 8, wherein the inert substrate comprises a fluoropolymer.

14. A method for bonding an inert substrate to a second substrate comprising:
    locating a reservoir of a liquid dielectric material adjacent to an electrode within a plasma reaction chamber of a dielectric barrier discharge system, the electrode being one of a pair of electrodes spaced apart from one another to form a discharge gap, and at least a portion of the liquid dielectric material comprising a polymer;
    disposing the inert substrate between the pair of electrodes within the discharge gap;
    establishing an electric potential between the pair of electrodes to produce a field of microdischarges across a surface of the liquid dielectric material, and to form a plasma that deposits resulting volatile byproducts of the liquid dielectric material onto a surface of the inert substrate; and
    bonding the surface of the inert substrate, on which the byproducts are deposited, to the second substrate.

15. The method of claim 14, wherein the polymer comprises a polyurethane.

16. The method of claim 14, further comprising heating or cooling the liquid dielectric material.

17. The method of claim 14, wherein the plasma reaction chamber is at atmospheric pressure when the plasma is formed.

18. The method of claim 14, wherein the second substrate comprises a second inert substrate having deposited volatile byproducts on at least a portion of a surface thereof.

19. The method of claim 14, wherein the bonding comprises using an adhesive.

20. The method of claim 19, wherein using an adhesive comprises applying the adhesive to at least one of the surface of the inert substrate, having the volatile byproducts deposited thereon, and a surface of the second substrate.

* * * * *